(12) United States Patent
Ardila

(10) Patent No.: US 9,056,064 B2
(45) Date of Patent: Jun. 16, 2015

(54) CONDITIONER COMPOSITION

(71) Applicant: Lilia Maria Ardila, Miami, FL (US)

(72) Inventor: Lilia Maria Ardila, Miami, FL (US)

( * ) Notice: Subject to any disclaimer, the term of this patent is extended or adjusted under 35 U.S.C. 154(b) by 0 days.

(21) Appl. No.: 13/908,285

(22) Filed: Jun. 3, 2013

(65) Prior Publication Data

US 2014/0352710 A1 Dec. 4, 2014

(51) Int. Cl.
| | | |
|---|---|---|
| *A61K 8/37* | (2006.01) | |
| *A61K 8/58* | (2006.01) | |
| *A61K 8/67* | (2006.01) | |
| *A61K 8/365* | (2006.01) | |
| *A61K 8/20* | (2006.01) | |
| *A61K 8/41* | (2006.01) | |
| *A61K 8/64* | (2006.01) | |
| *A61K 8/97* | (2006.01) | |
| *A61K 8/35* | (2006.01) | |
| *A61Q 5/12* | (2006.01) | |
| *A61Q 5/06* | (2006.01) | |
| *A45D 19/00* | (2006.01) | |
| *A61K 8/73* | (2006.01) | |

(52) U.S. Cl.
CPC . *A61K 8/97* (2013.01); *A61K 8/678* (2013.01); *A61K 8/35* (2013.01); *A61K 8/731* (2013.01); *A61K 8/64* (2013.01); *A61K 8/585* (2013.01); *A61K 8/20* (2013.01); *A61K 8/37* (2013.01); *A61K 8/416* (2013.01); *A61K 8/365* (2013.01); *A61Q 5/12* (2013.01); *A61Q 5/065* (2013.01); *A45D 2019/0041* (2013.01)

(58) Field of Classification Search
None
See application file for complete search history.

(56) References Cited

U.S. PATENT DOCUMENTS

| | | | |
|---|---|---|---|
| 2006/0018867 A1* | 1/2006 | Kawasaki et al. | 424/70.122 |
| 2008/0124286 A1* | 5/2008 | Lisson | 424/61 |
| 2010/0322887 A1* | 12/2010 | Aoki et al. | 424/70.1 |
| 2012/0058068 A1* | 3/2012 | van Gogh et al. | 424/70.9 |

* cited by examiner

*Primary Examiner* — David J Blanchard
*Assistant Examiner* — Sarah Chickos
(74) *Attorney, Agent, or Firm* — Christian Sanchelima

(57) ABSTRACT

A composition that rejuvenates hair by providing numerous functions for healthy, beautiful hair. The conditioner composition works best after shampooing the hair, whereby oil, grime, and debris are removed and the conditioner can maximize contact with the hair. The composition includes moisturizers that help retain moisture in the hair. The composition also serves as a reconstructor, penetrating the outer cuticle layer of the hair to the cortex and medulla layers of the hair, strengthening its structure through polymer crosslinking. The composition works as an acidity regulator. The composition includes heat absorbing polymers for shielding the hair against excessive heat caused by blow-dryers, curling irons, and hot rollers. The composition includes a surfactant to provide an additional layer to the hair for glossiness. The composition includes vitamins and nutrients efficacious for nourishing the hair follicle and hair strand itself.

2 Claims, 1 Drawing Sheet

100

| | INGREDIENT | VOLUME | FUNCTION |
|---|---|---|---|
| 102 | Tocopheryl | 15 ml | Provides vitamin E. Extracted from oxidized eggs, sunflower seed oil, and linseed oil |
| 104 | Benzophenone | 14 ml | Organic compound efficacious for regeneration of hair cells |
| 106 | Hydroxyethyl Cellulose | 25 ml | Thickener provides viscosity |
| 108 | Hydrolized Protein | 25 ml | Strengthens hair |
| 110 | Propyl Silanetriol | 10 ml | Skin and hair conditioning agent |
| 112 | Potassium Chloride | 10 ml | Cell and neuron regeneration |
| 114 | Soy Powder | 25 ml | Regeneration of cells and capillaries for potential hair growth |
| 116 | Cinchona Pubescens | 15 ml | Medicinal plant bark strengthens hair |
| 118 | Triglyceride | 15 ml | Revitalizes the capillaries of the hair. Fatty acids provide shine to the hair |
| 120 | Polyquaternium | 15 ml | Vitamin K, A, Carbon |
| 122 | Glycolic Acid | 50 ml | Used in the beauty industry to enhance the skin's appearance and texture, and provides amino acids, antioxidants, and vitamins to the hair |
| 124 | Parsley | 1 ml | Rich in many vitamins, including Vitamin C, B 12, K and A. These vitamins help heal split ends of hair damaged by excessive heat. |
| 126 | Alcohol | 10 ml | Solvent for dissolving solid ingredients |
| 128 | Garlic | 1 ml | Antioxidants and antibiotics |
| 130 | Water | 10 ml | Helps dissolve ingredients and regulate viscosity |

CONDITIONER COMPOSITION

BACKGROUND

The present invention is related to a conditioner composition that enhances the texture and appearance of hair.

Hair care refers to the parts of hygiene and cosmetology involving the hair on the human head. Hair care will differ according to the hair type and according to various processes that can be applied to hair. However, cleaning and strengthening the hair with compositions is an important facet of hair care.

It is well known that all natural ingredients regularly applied to the hair are vital to produce healthy and strong hair. There are certain hair compositions that work to provide vitamins and nutrients to hair, even after the hair has been cleaned.

Often, hair is washed as part of a shower or bathing with a shampoo, a specialized surfactant. Shampoos work by application of water and the shampoo to the hair for cleaning the hair. The shampoo breaks the surface tension of the water, allowing the hair to become soaked and residue to be removed. Conditioners are often used after shampooing to smooth down the cuticle layer of the hair, which can become roughened during the physical process of shampooing. Conditioners also work to strengthen the inner layers of each hair strand and add surfactants to the hair for enhanced shine.

Dandruff is the shedding of dead skin cells from the scalp. As the epidermal layer continually replaces itself, cells are pushed outward where they eventually die and flake off. For people with dandruff, skin cells may mature and be shed in 2-7 days, as opposed to around a month in people without dandruff. Moisturizing agents may help dry scalps to inhibit dandruff.

Hair coloring is the practice of changing the color of hair. Often, the dyes, bleaches, and thermal energy used to alter the hair's color can be destructive to the hair and scalp. In certain individuals, the use of hair coloring can result in allergic reaction and/or skin irritation. Hair that has been damaged by excessive exposure to chemicals is considered over-processed. This results in dry, rough and fragile hair. Vitamins help return the hair to its precolored state.

Split ends, known formally as trichoptilosis, happen when the protective cuticle has been stripped away from the ends of hair fibers. This condition involves a longitudinal splitting of the hair fiber. Any chemical or physical trauma, such as heat from blowers and hair irons may eventually lead to split ends. Vitamins A, K, and proteins help return the split ends to their prior condition by strengthening the cortex and medulla layers of the hair.

Hair loss, or androgenetic alopecia, is quite common. There is no cure, but there are many treatments for this male pattern hair loss. The range of treatments includes the application of lotions, shampoos, conditioners, to more sophisticated pills.

Genetics and health are additional factors for producing healthy hair and inhibiting the above mentioned hair problems. The living part of hair is under the scalp skin where the hair root is housed in the hair follicle. The entire follicle and root are fed by a vein, and blood carries nutrients to the follicle/root. Feeding this tissue with the proper vitamins, nutrients, and fats is vital to retaining healthy hair.

Typically, a hair conditioner is a hair care product that alters the texture and appearance of hair, while also incorporating healthy ingredients into the hair. There are numerous types of hair conditioner ingredients, differing in composition and functionality. The ingredients are composed with the objective of rejuvenating the hair and inhibiting hair problems.

Conditioners have been used in the hair care industry in the past, yet none with the present characteristics of the present invention. See U.S. Pat. Nos. 6,730,641; 8,420,065; and 20130039873.

For the foregoing reasons, there is a need for a conditioner composition that rejuvenates hair by adding all natural ingredients to the hair and scalp.

SUMMARY

The present invention is directed to a conditioner composition for enhancing the texture and appearance of hair. The composition helps rejuvenate hair by providing numerous functions for healthy, beautiful hair.

In some embodiments, the composition includes moisturizers that help retain moisture in the hair and scalp. Retaining moisture in the hair and scalp may help prevent dandruff. The composition also serves as a reconstructor, penetrating the outer cuticle layer of the hair to the cortex and medulla layers of the hair, strengthening its structure through polymer crosslinking. Those skilled in the art will recognize that the highly structural and organized cortex, or middle layer of the hair, is the primary source of mechanical strength and water uptake. The medulla is a disorganized and open area at the hair fiber's center. In some embodiments, the composition works as an acidity regulator, maintaining the conditioner's pH at about 3.5, which is a pH efficacious for detangling the hair.

In some embodiments, the composition includes heat absorbing polymers for shielding the hair against excessive heat caused by blow-dryers, curling irons, and hot rollers. These polymers also help inhibit peroxide and bleach damage to the hair. In some embodiments, the composition includes a surfactant to provide an additional layer to the hair for glossiness. The surfactant may include hydrophilic end that bond to the hydrophobic ends of the hairs keratin protein. In some embodiments, the composition includes vitamins and nutrients efficacious for nourishing the hair follicle and hair strand itself. In other embodiments, the cumulative effects of stimulation during application, and the eclectic ingredients may help restore hair with regular use.

In one embodiment, the conditioner composition is a 236 ml, or 8 oz liquid composition having sufficient viscosity to penetrate the hair and reach the scalp. The mixture is applied on to the hair after shampooing, preferably with a baby shampoo. Those skilled in the art will recognize that the conditioner composition may function best after shampooing the hair, whereby oil, grime, and debris are removed and the conditioner can maximize contact with the hair, from the hair follicle and throughout the hair shaft.

In one embodiment, the conditioner composition is composed of the following ingredients: tocopheryl, an organic compound extracted from oxidized eggs, linseed oil, and sunflower seed oil for providing vitamin E to the hair and scalp. A second ingredient includes an organic compound benzophenone, which may be extracted from a medicinal plant, and is efficacious for regeneration of hair cells. Another ingredient is hydroxyethyl cellulose is a gelling and thickening agent having no odor or flavor.

In some embodiments, the conditioner composition includes an additional ingredient of hydrolyzed proteins to form amino acids that serve to help grow hair. A further ingredient in the composition includes propyl silanetriol, a latex polymer that serves as a skin and hair conditioning agent, and is extracted from copper, zinc, and caviar. The composition comprises an additional ingredient of potassium chloride, a metal halide salt efficacious for brightening the hair and stimulating the capillaries.

In one embodiment, the composition includes the ingredient of soy powder, a vegetable protein used for regenerating the cells and capillaries, and helping to maybe grow hair. An additional ingredient includes, cinchono pubescens, a medicinal plant utilized for its bark's high quinine content. The composition further includes triglyceride, an ester derived from glycerol and three fatty acids, and utilized in the conditioner to help revitalize the capillaries of the hair.

In some embodiments, the conditioner composition includes an additional ingredient of polyquaternium, which are polycationic polymers used in the personal care industry that provide vitamins K, D, and carbon for growing hair and regeneration of the metabolism. Another ingredient in the composition includes glycolic acid, used in the beauty industry to enhance the skin's appearance and texture, and providing amino acids, antioxidants, and vitamins to the hair. The composition also includes an ingredient of parsley to help activate the hair follicles. Yet an additional ingredient is alcohol, an organic compound used as a solvent in the composition. Another ingredient is garlic. A final ingredient is water.

In one embodiment, the ingredients may be mixed through mechanical means without undergoing chemical bonding or other chemical change, so that each ingredient substance retains its own chemical properties and makeup. Nonetheless, the physical properties of the composition as a whole differ from the individual ingredients. In this manner, the quantities of each ingredient may be manipulated as desired to change the properties of the conditioner composition. For example, without limitation, increasing the ingredient hydroxyethyl cellulose may increase the viscosity of the composition.

The conditioner composition is used daily after shampooing, preferably with a baby shampoo. Those skilled in the art, in light of the present teachings, will recognize that life style changes such as, eating nutritious foods, avoiding excessive solar radiation, and daily vitamin intake of vitamins A, B complex, E, and Folic Acid may create a synergy with the composition to further enhance the appearance and texture of the hair.

An objective of the present invention is to rejuvenate the appearance of hair with a conditioner that uses all natural ingredients. The ingredients also serve to provide multivitamins and nutrients to the hair.

In yet another embodiment, the composition may help with hair growth, and may help inhibit dandruff due to the moisturizing capabilities.

DRAWINGS

These and other features, aspects, and advantages of the present invention will become better understood with regard to the following description, appended claims, and drawings where:

FIG. 1 is a table of the ingredients for the composition, in an exemplary embodiment of the present invention.

DESCRIPTION

One embodiment of a conditioner composition 100 is illustrated in FIG. 1, The conditioner composition 100 comprises of the following: about 15 ml tocopheryl 102; about 14 ml benzophenone 104; about 25 ml hydroxyethyl cellulose 106; about 20 ml hydrolyzed proteins 108; about 20 ml propyl silanetriol 110; about 10 ml potassium chloride 112; about 25 ml soy powder 114; about 15 ml *cinchona pubescens* 116; about 15 ml triglycerides 118; about 15 ml polyquaternium 120; about 50 ml glycolic acid 122; about 1 ml parsley 124; about 10 ml alcohol 126; about 1 ml garlic 128; and about 10 ml water 130.

The present invention is a conditioner composition 100 for enhancing hair with all natural ingredients. The composition 100 helps rejuvenate hair by providing numerous functions for healthy, beautiful hair. Those skilled in the art will recognize that the conditioner composition 100 may function best after shampooing the hair, whereby oil, grime, and debris are removed and the composition 100 can maximize contact with the hair, from the hair follicle and throughout the hair shaft.

In some embodiments, the composition 100 includes moisturizers that help retain moisture in the hair. Those skilled in the art will recognize that since a dry scalp is the genesis of dandruff, retaining moisture in the hair and scalp may help prevent dandruff.

The composition 100 also serves as a reconstructor, penetrating the outer cuticle layer of the hair to the cortex and medulla layers of the hair, strengthening its structure through polymer crosslinking. Those skilled in the art will recognize that the highly structural and organized cortex, or middle layer of the hair, is the primary source of mechanical strength and water uptake. The medulla is a disorganized and open area at the hair fiber's center.

In some embodiments, the composition 100 works as an acidity regulator, maintaining the conditioner's pH at about 3.5, which is a pH efficacious for detangling the hair. This pH balancing functionality is vital for healthy, shiny hair.

In some embodiments, split ends and discoloration may result from excessive heats and dyes on the hair. The composition 100 includes heat absorbing polymers for shielding the hair against excessive heat caused by blow-dryers, curling irons, and hot rollers. These polymers also help inhibit peroxide and bleach damage to the hair.

In some embodiments, the composition 100 includes a surfactant to provide an additional layer to the hair. This layer adds gloss and shininess to the hair. The surfactant may attach to the hair with a hydrophilic end that bonds to the hydrophobic ends of the hairs keratin protein.

In some embodiments, the composition 100 includes vitamins and nutrients efficacious for nourishing the hair follicle and hair strand itself. The vitamins include Vitamins E, K, B, A, and folic acids. In other embodiments, the cumulative effects of stimulation during application, and the eclectic ingredients may help restore hair with regular use.

In one embodiment, the conditioner composition 100 is a 236 ml, or 8 oz liquid composition 100 having sufficient viscosity to penetrate the hair and reach the scalp. The mixture is applied on to the hair after shampooing, preferably with a baby shampoo. However, in other embodiments, an all-purpose shampoo may be sufficient to preclean the hair prior to applying the conditioner composition 100. After application of the conditioner composition 100, thermal energy in the form of a blow dryer or sunlight helps activate the ingredients of the composition 100 on the hair.

In one embodiment, the conditioner composition 100 is composed of the following ingredients: 15 ml tocopheryl 102, an organic compound extracted from oxidized eggs, linseed oil, and sunflower seed oil for providing vitamin E to the hair and scalp. The egg may be enriched with cholesterol and be dried and oxidized for up to twelve months. A second ingredient includes 14 ml of the organic compound benzophenone 104, a white powder which may be extracted from a medicinal plant, and is efficacious for regeneration of hair cells. The benzophenone is produced in India and America. Another ingredient is 25 ml of hydroxyethyl cellulose 106, which is a gelling and thickening agent. The hydroxyethyl cellulose 106 has no odor or flavor.

In some embodiments, the conditioner composition 100 includes an additional ingredient of 20 ml hydrolyzed proteins 108 to form amino acids that serve to help grow hair. A further ingredient in the composition 100 includes 10 ml propyl silanetriol 110, a latex polymer that serves as a skin and hair conditioning agent, and is extracted from copper, zinc, and caviar. The composition 100 comprises an additional ingredient of 10 ml potassium chloride 112, a metal halide salt efficacious for brightening the hair and stimulating the capillaries. The minerals of potassium and chloride are essential for shiny hair and stimulating the capillaries.

In one embodiment, the composition 100 includes the ingredient of 25 ml soy powder 114, a vegetable protein used for regenerating the cells and capillaries, and helping to maybe grow hair. An additional ingredient includes, 15 ml cinchono pubescens 116, a medicinal plant utilized for its bark's high quinine content. The bark of the cinchono pubescens 116 provides quinine and other ingredients efficacious for improving hair appearance and strength. The composition 100 further includes 15 ml triglyceride 118, an ester derived from glycerol and three fatty acids, and utilized in the conditioner to help revitalize the capillaries of the hair. The fatty acids provide shine and luster to the hair.

In some embodiments, the conditioner composition 100 includes an additional ingredient of 15 ml polyquaternium 120, which is polycationic polymer used in the personal care industry. The polyquaternium provides vitamins K, D, and carbon for growing hair and regeneration of the metabolism. Those skilled in the art will recognize that polyquaternium is the international nomenclature for cosmetic ingredients designation for several polycationic polymers that are used in the personal care industry. There are various types of polyquaternium which may be utilized for the composition 100. For example, without limitation, polyquaternium-1 includes Ethanol, 2,2',2"-nitrilotris-, polymer with 1,4-dichloro-2-butene and N,N,N',N'-tetramethyl-2-butene-1,4-diamine, while polyquaternium-28 includes copolymer of vinylpyrrolidone and methacrylamidopropyl trimethylammonium. Each type of polyquaternium provides different vitamins, nutrients, and other benefits. Another ingredient in the composition 100 includes 50 ml glycolic acid 122, used in the beauty industry to enhance the skin's appearance and texture, and providing amino acids, antioxidants, and vitamins to the hair.

In on embodiment, the composition 100 also includes an ingredient of 1 ml parsley 124 to help activate the hair follicles. The hair benefits from parsley because it is rich in many vitamins, including Vitamin C, B 12, K and A. These vitamins help heal split ends of hair damaged by excessive heat. Yet an additional ingredient is 10 ml alcohol 126, an organic compound. The alcohol 126 serves as a solvent to help dissolve the other solid ingredients. An additional ingredient is 1 ml of garlic 128, which contains antibiotics and has many antioxidants for the hair to benefit from. A final ingredient is 10 ml water 130 to help dissolve the ingredients and reduce viscosity of the composition 100. In the present invention, the amounts and phases of the ingredients may be manipulated to produce varying types of hair conditioners.

In one embodiment, the ingredients may be mixed through mechanical means without undergoing chemical bonding or other chemical change, so that each ingredient substance retains its own chemical properties and makeup. Nonetheless, the physical properties of the composition 100 as a whole differ from the individual ingredients. In this manner, the quantities of each ingredient may be manipulated as desired to change the properties of the conditioner composition 100. For example, without limitation, increasing the ingredient hydroxyethyl cellulose 108 may increase the viscosity of the composition 100.

The conditioner composition 100 is used daily after shampooing, preferably with a baby shampoo. Those skilled in the art, in light of the present teachings, will recognize that life style changes such as, eating nutritious foods, avoiding excessive solar radiation, and daily vitamin intake of vitamins A, B complex, E, and Folic Acid may create a synergy with the composition 100 to further enhance the appearance and texture of the hair.

The composition 100 is only effective if applied properly. In operation, the composition 100 is most effective when applied after shampooing. A method of applying the composition 100 includes a first Step of rinsing hair with a liquid, such as water. The temperature of the water is not decisive on the effectiveness of the composition 100. A next Step includes, applying the shampoo to the hair and then massaging the shampoo on the scalp, then leaving the shampoo on the scalp for a predetermined duration. In this manner, residue is removed from the hair in preparation for the composition 100. This can be followed by the Step of rinsing a substantial amount of the shampoo from the hair. Massaging by the hands and a steady stream of water are helpful in this. The next Step includes applying the composition 100 to the hair and then massaging the composition 100 onto the scalp, then leaving the composition 100 on the scalp for a predetermined duration. Another Step is rinsing a substantial amount of the composition 100 from the hair. A final Step includes applying thermal energy to the hair. The thermal energy includes an air dryer or the sun. The thermal energy help activate the ingredients to work on the hair. These steps are repeated daily for optimal results.

Thus the reader will see that the conditioner composition 100 provides an efficient process for rejuvenating hair with all natural ingredients.

While the inventor's above description contains many specificities, these should not be construed as limitations on the scope, but rather as an exemplification of several preferred embodiments thereof. Many other variations are possible. For example, the conditioner composition could be used to condition fur on animals, since the physical properties of hair are similar for both humans and animals. Accordingly, the scope should be determined not by the embodiments illustrated, but by the appended claims and their legal equivalents.

What is claimed is:

1. A composition for enhancing the texture and appearance of hair, consisting of:
   approximately 6.1% of tocopheryl by weight of the composition;
   approximately 5.7% of benzophenone by weight of the composition;
   approximately 10.2% of hydroxyethyl cellulose by weight of the composition;
   approximately 10.2% of hydrolyzed protein by weight of the composition;
   approximately 4.1% of propyl silanetriol by weight of the composition;
   approximately 4.1% of potassium chloride by weight of the composition;
   approximately 10.2% of soy powder by weight of the composition;
   approximately 6.1% of *cinchona pubescens* by weight of the composition;

approximately 6.1% of triglycerides by weight of the composition;
approximately 6.1% of polyquaternium by weight of the composition;
approximately 20.3% of glycolic acid by weight of the composition;
approximately 0.4% of parsley by weight of the composition;
approximately 4.1% of alcohol by weight of the composition;
approximately 0.4% of garlic by weight of the composition; and
approximately 4.1% of water by weight of the composition.

2. A composition for enhancing the texture and appearance of hair, consisting of:
a tocopheryl from 4.1% to 8.1% by weight of the composition;
a benzophenone from 4.1% to 8.1% by weight of the composition;
a hydroxyethyl cellulose from 8.1% to 12.2% by weight of the composition;
a hydrolyzed protein from 6.1% to 10.2% by weight of the composition;
a propyl silanetriol from 4.1% to 10.2% by weight of the composition;
a potassium chloride from 2% to 6.1% by weight of the composition;
a soy powder from 8.1% to 12.2% by weight of the composition;
a *cinchona pubescens* from 4.1% to 8.1% by weight of the composition;
a triglycerides from 4.1% to 8.1% by weight of the composition;
a polyquaternium from 4.1% to 8.1% by weight of the composition;
a glycolic acid from 18% to 23% by weight of the composition;
a parsley from 0.2% to 0.8% by weight of the composition;
an alcohol from 2% to 6.1% by weight of the composition;
a garlic from 0.2% to 0.8% by weight of the composition; and
a water from 2% to 6.1% by weight of the composition.

* * * * *